(12) United States Patent   (10) Patent No.: US 9,364,244 B2
Amis et al.   (45) Date of Patent: Jun. 14, 2016

(54) RECONSTRUCTION OF ANTERIOR CRUCIATE LIGAMENTS

(71) Applicant: Imperial Innovations Ltd., London (GB)

(72) Inventors: Andrew Amis, Middlesex (GB); Andrew Edwards, Surrey (GB)

(73) Assignee: Imperial Innovations Ltd. (GB)

( * ) Notice: Subject to any disclaimer, the term of this patent is extended or adjusted under 35 U.S.C. 154(b) by 0 days.

(21) Appl. No.: 14/850,017

(22) Filed: Sep. 10, 2015

(65) Prior Publication Data

US 2015/0374390 A1   Dec. 31, 2015

Related U.S. Application Data

(63) Continuation of application No. 13/897,635, filed on May 20, 2013, now abandoned, which is a continuation of application No. 12/225,460, filed as application No. PCT/GB2007/000767 on Mar. 5, 2007, now Pat. No. 8,444,652.

(30) Foreign Application Priority Data

Mar. 23, 2006 (GB) .................................. 0605817.6

(51) Int. Cl.
*A61B 17/17* (2006.01)
*A61F 2/08* (2006.01)
*A61B 19/00* (2006.01)

(52) U.S. Cl.
CPC .......... *A61B 17/1764* (2013.01); *A61B 17/1714* (2013.01); *A61B 19/5244* (2013.01); *A61F 2/0805* (2013.01); *A61B 19/46* (2013.01); *A61B 2019/505* (2013.01); *A61B 2019/5483* (2013.01)

(58) Field of Classification Search
CPC .................................................. A61B 17/1764
See application file for complete search history.

(56) References Cited

U.S. PATENT DOCUMENTS

| | | | | |
|---|---|---|---|---|
| 6,187,011 B1 * | 2/2001 | Torrie | ................. | A61B 17/1714 606/104 |
| 6,254,605 B1 * | 7/2001 | Howell | ............... | A61B 17/1714 606/86 R |
| 6,918,916 B2 * | 7/2005 | Gobel | ................. | A61B 17/1714 606/96 |
| 7,473,259 B2 * | 1/2009 | Jacobs | ............... | A61B 17/0482 606/148 |
| 8,444,652 B2 * | 5/2013 | Amis | ................. | A61B 17/1714 606/88 |

* cited by examiner

*Primary Examiner* — Andrew Yang
(74) *Attorney, Agent, or Firm* — Norman F. Hainer, Jr.

(57) ABSTRACT

Apparatus for locating an attachment position for a reconstructed anterior cruciate ligament on an attachment surface of a bone comprises locating means 51, 61 arranged to locate at least one reference surface 4 of the bone and guide means 53, 54 arranged to define the attachment position in two dimensions on the attachment surface relative to the reference surface.

24 Claims, 7 Drawing Sheets

RECONSTRUCTION OF ANTERIOR CRUCIATE LIGAMENTS

CROSS-REFERENCE TO RELATED APPLICATIONS

This application is a continuation of U.S. patent application Ser. No. 13/897,635 filed on May 20, 2013, which is a continuation of U.S. Pat. No. 8,444,652 filed on Dec. 4, 2008, which is a national stage entry of PCT Appl. No. PCT/GB2007/000767 filed Mar. 5, 2007, which claimed benefit of G.B. Appl. Serial No. 0605817.6 filed Mar. 23, 2006, all of the disclosures of which are incorporated herein by reference in their entirety.

FIELD OF THE INVENTION

The present invention relates to the reconstruction of the anterior cruciate ligament, and in particular to the location of attachment points for the reconstructed ligament.

BACKGROUND TO THE INVENTION

The anterior cruciate ligament (ACL) originates from the medial aspect of the lateral femoral condyle and is inserted into the tibial plateau medial to the anterior horn of the lateral meniscus.

The ACL is a strong structure that has an important role in stabilising the knee. It is often injured, especially during sports activities, and does not usually heal. Because of these factors, it is usual for a ruptured ACL to be treated by reconstructive surgery, when a tendon graft is usually used to replace the damaged ACL. In conventional ACL reconstruction, a single graft structure is made: either a strip of the patellar tendon, or else a composite structure consisting of usually four strands of hamstrings tendons are used. This graft is placed inside the knee joint, replacing the ACL. It is hoped that it will heal in place and remodel into a new ACL.

In order to fix the new graft in place, it is usual for the surgeon to drill a graft tunnel at the attachment site in both the femur and tibia. These tunnels are usually placed at the anatomical attachment areas of the damaged ACL. During surgery, the graft is pulled into these tunnels and secured; many devices have been developed to anchor these grafts.

The principal reason for ACL reconstructive surgery to fail is malplacement of the graft fixation tunnels. That occurs because the ACL is placed awkwardly within the knee joint, and it is difficult to judge the exact positions needed, even when looking through a modern arthroscopic camera system. Recognising this, surgical instruments have evolved to try to make the choice of tunnel position less subjective, but that approach has not developed to the point where errors are avoided.

A further factor is that the ACL has a complex fibre bundle structure, with many fibre fascicles that attach over quite large areas on the bone surfaces. This leads to individual fibres having different lengths. They also have different patterns of tightening and slackening as the knee flexes and extends, or as the tibia rotates about its long axis. Recognising this, there has recently been a development of 'double-bundle' reconstruction methods. This usually involves making two tunnels in each bone, and using two grafts. These are a crude approximation of two main areas of fibres in the cross-section of the ACL [Fakhry G &. Girgis. T. *Clin Orthop* 1975; 106]. These bundles are normally called the 'anteromedial' AM bundle (or AMB) and 'posterolateral' PL bundle (or PLB). These names relate to their relative positions of attachment to the tibial plateau. In general, it has been found that the PLB tightens as the knee is extended, while the AMB is tightest in the flexed knee [Xerogeanes J W. et al. Knee Surg Sports Traumatol Arthrosc 1995; 3: 9-13, Sakane M. *J Orthop Res.* 1997; 15: 285-293, Bach J M. et al. *J Biomech.* 1997; 30: 281-283]. Thus, they have distinct stabilising roles. The underlying principle of double-bundle surgery is that it more closely reproduces the natural ACL anatomy, and also functions closer to the natural ligament than does a single-bundle reconstruction. Isometric reconstructions reproduce the anteromedial bundle, but the knee needs stability in the functional posture, which is when it is weight-bearing near extension, ie the posterolateral bundle is then needed.

Surgical methods of ACL reconstruction following injury have developed considerably over the last 15 years. Primary repair and extra-articular procedures have failed to reproduce satisfactory stability of the knee [Grontvedt T. et al. *J Bone Joint Surg [Am]* 1996; 78-A: 159-68] and the use of prosthetic ligaments has been abandoned [Frank C. & Jackson D W. *J Bone Joint Surg [Am]* 1997; 79-A:1556-76]. These techniques have been superseded by reconstruction with an intraarticular graft. Hence, the current surgical approach is by anatomical reconstruction using a biological tissue autograft. The bone-patellar tendon-bone graft B-PT-B has given good clinical results [Corry I. S. et al. *Am J Sports Med* 1999; 27:444-53] but morbidity at the donor site [Christen B. & Jakob R P. *J Bone Joint Surg [Br]* 1992; 74-B:617-19, Kartus J. et al. *Knee Surg Sports Traumatol Arthrosc* 1997; 5:222-8] has prompted many surgeons to favour a four-strand hamstring graft, usually using the tendons of semitendinosus and gracilis doubled.

Radford and Amis [*J Bone Joint Surg Br* 1990; 72: 1038-1043] reported that a double-bundle reconstruction controlled anterior laxity better than single-bundle reconstructions, across the range of knee flexion. Yagi et al [*Am J Sports Med.* 2002; 30: 660-666] reported finding the biomechanical outcome, especially in rotatory loading, may be superior with double bundle reconstructions compared to single bundle reconstructions, and Mae et al [*Arthroscopy* 2001; 17: 708-716] similarly found better antero-posterior stability using a two femoral socket technique when compared to the standard single socket ACL reconstruction. Mommersteeg et al [*J Anat.* 1995; 187: 461-471] suggested that successful ACL reconstruction may not be achieved simply by replacing one bundle. Conventional endoscopic ACL graft placement does not always control tibial rotation laxity, leaving a residual 'mini-pivot' [Bull A M J. et al. J Bone Jt Surg 84Br: 1075-1081, 2002]. The realisation that anterior laxity is not an adequate measure of success of an ACL reconstruction, and that rotatory laxity is important has led to a sudden widespread interest in double-bundle methods, [Amis A A et al. Operative Methods in Sports Med 15; 29-35, 2005].

Race & Amis developed a double-bundle PCL reconstruction method [J Bone Jt Surg 80B, 1998; 173-179] that was widely adopted, partly because it was also shown clearly that: a) the PCL was not an isometric ligament; b) that isometric PCL reconstructions gave less effective control of tibial posterior laxity.

ACL reconstruction aims to recreate the exact mechanical properties of the injured ligament and restore normal function to the knee. Currently, this cannot be achieved. Biomechanical testing of ligament reconstructions in the laboratory has been used widely in attempts to recreate these mechanical properties. Although the ultimate load to failure of the B-PT-B and that of the four-strand hamstring graft exceed those reported for the intact ACL, it is accepted that in the early postoperative period it is the fixation of the graft which is the weak link [Kurosaka M. et al *Am J Sports Med* 1987; 15:225-9].

ACL fixation may be either mechanical or biological. The emphasis on accelerated programmes of rehabilitation and demands for a rapid return of function necessitate secure mechanical fixation in the early post-operative period before biological fixation has occurred by healing in the graft tunnel.

As ACL reconstruction techniques evolve, an accurate and useful description of the attachment anatomy is required in order to design instruments capable of placing graft tunnels so that their entrances are in anatomically correct locations, within the ACL attachments. Anatomical descriptions of the attachment anatomy of the two bundles of the ACL using methods that can be employed clinically are lacking. An accurate map of the attachment of the ACL on the femur is key for the development of double bundle techniques and in outcome studies to describe optimal and suboptimal positions for graft placement.

The importance of femoral tunnel placement in ACL reconstruction has previously been reported with respect to a single graft bundle technique [Amis A A. & Jakob R P. *Knee Surg Sports Traumatol Arthrosc* 1998; 6 Suppl 1: S2-12]. Sommer [*Knee Surg Sports Traumatol Arthrosc* 2000; 8: 207-213] found a significant correlation between the femoral single bundle placement and the International Knee Documentation Committee IKDC score. As the placement of the graft as seen on X-ray moved away from the most isometric point, the IKDC scores decreased. It will be just as critical to achieve optimum graft placement in the double bundle technique as it is in the single bundle technique.

EP0361756 describes a device that measures changes in distance between chosen points on femur and tibia. It does not assist the surgeon in identifying anatomical locations for graft tunnels; instead it helps to identify points that are a constant distance apart when the knee flexes i.e. points that are "isometric".

EP0440991 A1 also refers to finding an 'isometric' point. It also describes a new type of drill for making a hole of known depth. A tibial drill guide is also described. However this device relies entirely on the surgeon's judgement for placement within the knee. A feature of this device is that the guide barrel can slide towards the bone until its sharp tip engages the bone, thereby stabilising the drill guide in the chosen position. This feature is common to many types of drill guides.

EP0495487 A2 discloses a drill that, instead of just boring out a hole through the bone, cuts it out as a solid core, for use elsewhere in the operation. A "guide for locating a pilot hole on the femoral condyle" is cited but this is a bone coring/drilling method, there is no assistance given to place the tunnel accurately.

U.S. Pat. No. 4,883,048 discloses a feature that is used widely, namely the use of an arcuate feature to allow the drill to be guided through a tube to a fixed point from a range of directions. However, the choice of precisely where to drill is still surgeon-dependent; the instrument does not locate the optimal site.

U.S. Pat. No. 5,269,786 and U.S. Pat. No. 5,409,494 use the arcuate feature. They describe a drill guide that does aim to locate the correct place for a graft tunnel, but it does so by locating on another ligament, the PCL, and does not utilise bony features. The PCL is a soft tissue structure and so is inherently inaccurate as a datum.

In U.S. Pat. No. 6,019,767 and U.S. Pat. No. 5,300,077 is described a device whose principle is that the axis of the drill guide is aligned parallel to the probe tip that rests on the roof of the femoral intercondylar notch. Thus, it ensures that the graft will not impinge against the notch roof. It therefore locates the tibial drill hole in relation to the femur. It does not address the femoral tunnel location.

U.S. Pat. No. 5,350,383 also uses the arcuate feature but attempts to 'invert' the moving feature. Once again the surgeon judges where to place the drill target.

U.S. Pat. Nos. 5,520,693, 6,352,538 and 6,878,150 give a device that has a tongue protruding from the body of the drill guide that locates on an edge of the bone, ensuring that the drill axis is located a certain distance from that edge. However, it does not identify where to go along the edge of the bone—only one direction/dimension is controlled. The surgeon usually places the probe or tongue at a chosen "o'clock" position in the femoral notch.

U.S. Pat. No. 5,603,716 describes a means of locating tunnel positions using an aimer referenced to anatomical structures within the knee. It is a method for drilling a socket in the tibia but it does nothing to identify exactly where the socket should be situated.

The devices provided by U.S. Pat. No. 6,254,604 and U.S. Pat. No. 6,254,605 are similar to U.S. Pat. No. 5,300,077 but the latter adds a removable guide bar to provide visual alignment in the coronal plane. This principle being that, if the bar is held horizontal, then the drill guide will slant across the tibia in a preferred orientation. This guides the tunnel orientation.

The basis of the device in EP0384098 is that it combines two drill guides in one instrument, with a fixed relationship between them, intending to create tibial and femoral tunnels at the "correct" places in the knee. It has a hook that locates over the posterior edge of the tibia. The tibial tunnel is always on the midline while the femoral tunnel guide can be swung to left or right for an oblique tunnel in left or right knees. The femoral tunnel is located in relation to the hook on the tibia.

GB 2 268 688 provides a device for locating tibial tunnels. The device is simply placed into the knee at an angle to the midline plane, so that its probe passes to one side of the patellar tendon. Bends are introduced into the instrument, to allow the probe tip to be straight along the midline plane, while the body of the drill guide is held at an oblique plane outside the knee.

U.S. Pat. No. 4,257,411 describes a drill guide adapted to clamp securely onto the bone. It has no features that locate the tunnel in relation to the anatomy.

U.S. Pat. No. 5,112,337 describes a further device for tibial tunnel placement. It relies on surgeon's judgement of where to drill the hole, by placing a target tip. It has an arcuate adjustment to vary the tunnel orientation. It also allows the drill guide to slide until its tip engages the bone. The sliding drill guide has length marks so that the surgeon can choose a desired tunnel length.

U.S. Pat. No. 4,823,780, EP0162027 and U.S. Des 289,436 provide a device for making tunnels that are in a fixed relationship in space. The device requires surgeon's judgement for placing it correctly in the knee, it has no location features.

A study of graft tunnel positions following endoscopic single-bundle ACL reconstructions performed by surgeons in Europe revealed a need for major improvement in ACL reconstruction instrumentation, a principal aim being to reduce the subjective element of judgement of instrument positioning prior to drilling bone tunnels [Kohn D. et al in Knee Surg. Sports Traumatol. Arthrosc. 6 Suppl 1: S13-S15, 1998].

The present invention aims to address two unmet clinical needs: Firstly, the frequent failure of ACL reconstructions, which is mostly caused by misplacement of the graft tunnels and, secondly, the residual rotatory laxity remaining after conventional endoscopic ACL reconstruction of the knee.

The inventors have measured the location and extent of the femoral and tibial attachments of the ACL. A range of different measurement systems has been used, reflecting methods published previously. Some of the measurement methods have been modified in order to make them more relevant to arthroscopic surgery. This work included measurement of the centres of both the entire ligament and also of the individual fibre bundle attachments. The attachment locations have been related to bone landmarks suitable for locating instruments.

SUMMARY OF THE INVENTION

The present invention provides apparatus for locating an attachment position for a reconstructed anterior cruciate ligament on an attachment surface of a bone, the apparatus comprising locating means arranged to locate at least one reference surface of the bone and guide means arranged to define the attachment position in two dimensions on the attachment surface relative to the reference surface.

The present invention further provides a method of locating an attachment position for a reconstructed anterior cruciate ligament on an attachment surface of a bone, the method comprising locating at least one reference surface of the bone and defining the attachment position in two dimensions on the attachment surface relative to the reference surface.

Some embodiments of the present invention provide novel instrument designs based upon detailed anatomical measurements of the attachment locations of the AM and PL bundles of the ACL, which are useful for both single and double-bundle ACL graft reconstructions.

Single-bundle ACL reconstruction is a difficult procedure. In double-bundle methods, the need for four tunnels creates greater potential for surgical error. Some embodiments of this invention provide accurate instrumentation, which can reduce or eliminate subjective judgement regarding tunnel placement and facilitates double-bundle ACL reconstruction.

This invention relates in part to advancing the art of double-bundle reconstruction surgery. It recognises that it is essential to know the locations of the bundle attachments, in order to be able to design instruments that can guide the surgeon to the correct tunnel sites. This invention also applies to the development of software for surgical guidance 'navigation' systems.

It is difficult to provide the relevant geometrical information, because of the complex shape of the internal cavity of the knee joint. As a result of taking many measurements on cadaveric specimens, this invention provides several different systems for locating the bundle attachment points. In particular, these measurements are related to visually identifiable features of the bony anatomy. This is important because the bony anatomy will usually remain with only small changes after ACL injury, whereas the ACL itself will often disappear if there is a delay between injury and surgery. These measurements, therefore, provide the basis for designing guidance instruments that locate onto, or in relation to, bony landmarks. This provides a greater degree of reproducibility than with currently available instruments and avoids subjective human errors of tunnel placement.

It should be recognised that the measurement data is useful not only for placing the graft tunnels in double-bundle reconstructions but also for conventional single-bundle procedures. Measurement data for the centres of the whole ACL attachments to both femur and tibia is used in novel instrument design.

In one embodiment, the invention provides instruments that make use of anatomical measurement data and the principle of locating off of bony landmarks. While it is normal to locate conventional femoral drill guides this way, it only works in one direction, not in the necessary two-dimensional way. One instrument used in the art is called an 'offset drill guide' that has a hook-like extension that locates over a ridge across the back of the femur. The body of the instrument then guides a pin to the desired tunnel location a fixed distance away from the ridge (the offset). It does not, however, control where along this ridge the surgeon may choose to place the guide.

For the tibia, a further provision of this invention is a surgical instrument having a probe that extends posteriorly through the knee, and is bent downwards at its tip. This provides a hook that can locate over a transverse ridge, where the tibial surface slopes down to the attachment point of the posterior cruciate ligament PCL. This feature controls the anterior-posterior position i.e. front to back. The medial-lateral position i.e. left-right when looking into the front of a left knee is then controlled by locating the side of the probe against a prominent bony spur called the medial tibial tubercle. Thus, this instrument controls the tunnel position in two dimensions across the tibial plateau.

For the femur, a further embodiment is an instrument with a probe that locates over the posterior transverse ridge, but which also extends around the surface of the intercondylar notch where the ACL attaches. This also locates in two dimensions, avoiding subjective assessments of where to place the tunnel around the notch.

A further aspect of the invention is that the surgeon usually looks at what is happening via an arthroscope. While that gives a magnified view, it is one-dimensional, so that depth perception is limited. It also means that the surgeon loses sight of how the field of view relates to the overall alignment of the limb segments, the thigh and shank. This situation may cause instruments to be used in a skewed orientation, particularly because the instruments usually enter the knee in a slanting orientation, passing either side of the large centrally-placed patellar tendon. In order to avoid such misorientation, the invention incorporates deviations or bends in the shafts of the location instruments so that the surgeon can hold them in line with the limb segments whilst the 'working' tips are at the correct posture within the knee joint.

Another aspect of the invention is that the instrument shafts may incorporate alignment rods that aid alignment, e.g. by being held parallel to the limb.

Yet another aspect of the invention is that the measurement data enables a range of instrument sizes of the relevant dimensions to be designed to suit the range of knee sizes that exist among the general population. This feature enables accurate tunnel placement regardless of individual joint dimensions.

An embodiment of the invention is an instrument for locating an attachment position for a reconstructed ACL in a femur. The instrument includes a handle, a side piece with a hole in the side piece that defines the attachment position for the reconstructed ACL, and a tip. The side piece may include a first surface shaped to fit at least in part against a lateral side wall of an intercondylar notch to locate the instrument relative to the femur, and a second surface configured to contact a roof of the intercondylar notch at the same time the first surface is at least in part against the lateral side wall of the intercondylar notch to locate the instrument relative to the femur. The tip may be arranged to wrap around a back surface of a condyle of the femur and contact the back surface of the condyle at the same time the first surface is at least in part against the lateral side wall of the intercondylar notch and the second surface is contacting the roof of the intercondylar notch to locate the instrument relative to the femur.

Another embodiment is an instrument for locating an attachment position for a reconstructed ACL in a femur. The instrument includes a handle, a side piece with a hole in the side piece that defines the attachment position for the reconstructed ACL, and a tip. The side piece may also include a first surface shaped to fit at least in part against a lateral side wall of an intercondylar notch to locate the instrument relative to the femur, and a second surface configured to contact a roof of the intercondylar notch at the same time the first surface is at least in part against the lateral side wall of the intercondylar notch to locate the instrument relative to the femur. The tip may have a contact surface directed at least in part toward the second surface such that at least part of the contact surface forms an angle of less than 180 degrees with the second surface, wherein the contact surface is configured to contact a part of the femur at the same time the first surface is at least in part against the lateral side wall of the intercondylar notch and the second surface is contacting the roof of the intercondylar notch to locate the instrument relative to the femur.

Still another embodiment is a method of locating an attachment position for a reconstructed ACL in a femur. The method may include passing a tip of a locating instrument around a condyle of the femur by moving the locating instrument distally and laterally, moving the locating instrument proximally to bring the tip of the locating instrument into contact with a back surface of the condyle, contacting a first surface of a side piece of the locating instrument against a lateral side wall of an intercondylar notch, and contacting a second surface of the side piece of the locating instrument against a roof of the intercondylar notch at the same time the first surface is contacting the lateral side wall of the intercondylar notch and the tip of the locating instrument is contacting the back surface of the condyle to locate the instrument relative to the femur.

Preferred embodiments of the present invention will now be described by way of example only with reference to the accompanying drawings.

DESCRIPTION OF PREFERRED EMBODIMENTS

Figure 1:
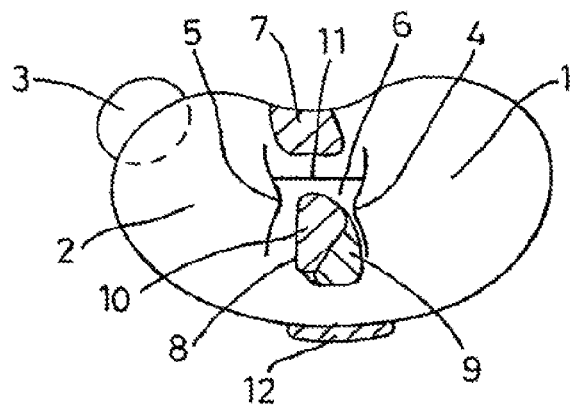
FIG. 1 is a top view of a tibial plateau.

FIG. 1 is a simplified representation of the anatomy of the tibial plateau that is the top surface of the tibia. This looks down onto the tibial plateau of a right knee: anterior is at the bottom, posterior at the top, medial to the right and lateral to the left. The main articular bearing areas are the medial tibial plateau 1 and the lateral tibial plateau 2. The head of the fibula 3 is postero-lateral. The plateaux 1, 2 are limited in extent towards the centre of the tibia when they reach bony ridges: the medial tibial spinous process 4, and the lateral tibial spinous process 5. There is a trough, or fossa 6, between the spines 4, 5, the interspinous fossa. Posteriorly, the PCL attaches in a posterior attachment area 7 between the medial and lateral plateaux 1, 2. Anteriorly, the ACL attaches in an anterior attachment area 8 within the interspinous fossa 6. This attachment 8 may be divided into two attachment areas, where separate fibre bundle attachments are located: one in the anteromedial bundle attachment area 9 and one in the posterolateral attachment area 10. A transverse inter-spinous ridge 11 passes between the medial and lateral spinous processes 4, 5, and forms a transition between anterior and posterior-facing slopes on the surface of the bone. The patellar tendon 12 is a strong structure passing vertically from the tibia to the patella at the front of the knee.

Figure 2:
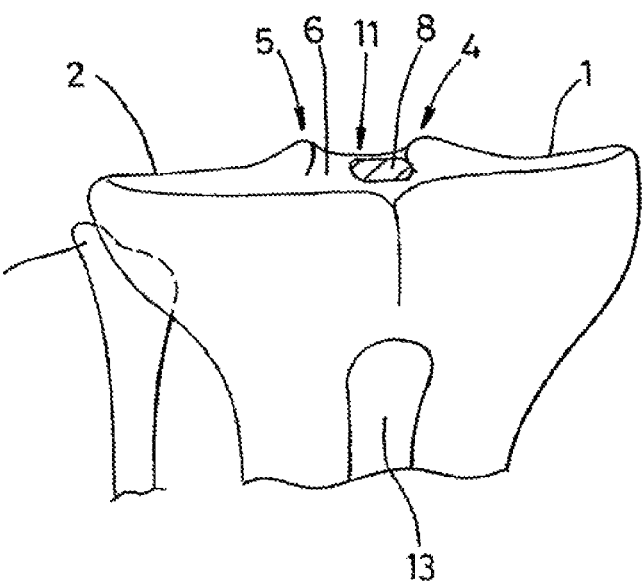
FIG. 2 is an anterior-posterior view of a proximal tibia.

FIG. 2 shows an anterior-posterior view of the proximal tibia, with the medial 1 and lateral 2 plateaux, the medial 4 and lateral 5 spinous processes, the inter-spinous or, sometimes, "inter-condylar" fossa 6, that contains the ACL attachment 8. The transverse inter-spinous ridge 11 forms the central 'skyline'. The patella tendon attaches distally, to the tibial tubercle 13, and has been omitted from this view.

Figure 3:
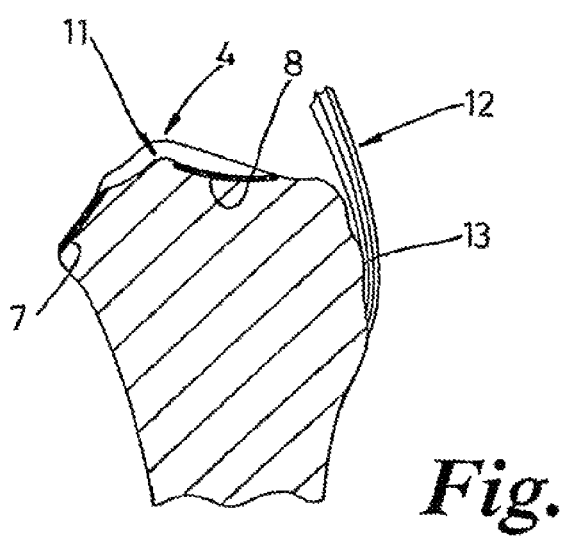
FIG. 3 is a sectioned lateral-medial view of the proximal tibia.

FIG. 3 shows a lateral-medial view of the tibia after it has been sectioned in a central sagittal plane. The PCL attaches posteriorly in a PCL attachment area 7, the ACL anteriorly in the ACL attachment area 8. Between the ACL and PCL attachments is the transverse inter-spinous ridge 11. The medial spinous process 4 is visible beyond the sectioning plane. The tibial tubercle 13 is prominent anteriorly and the patellar tendon 12 passes up to the patella.

Figure 4:
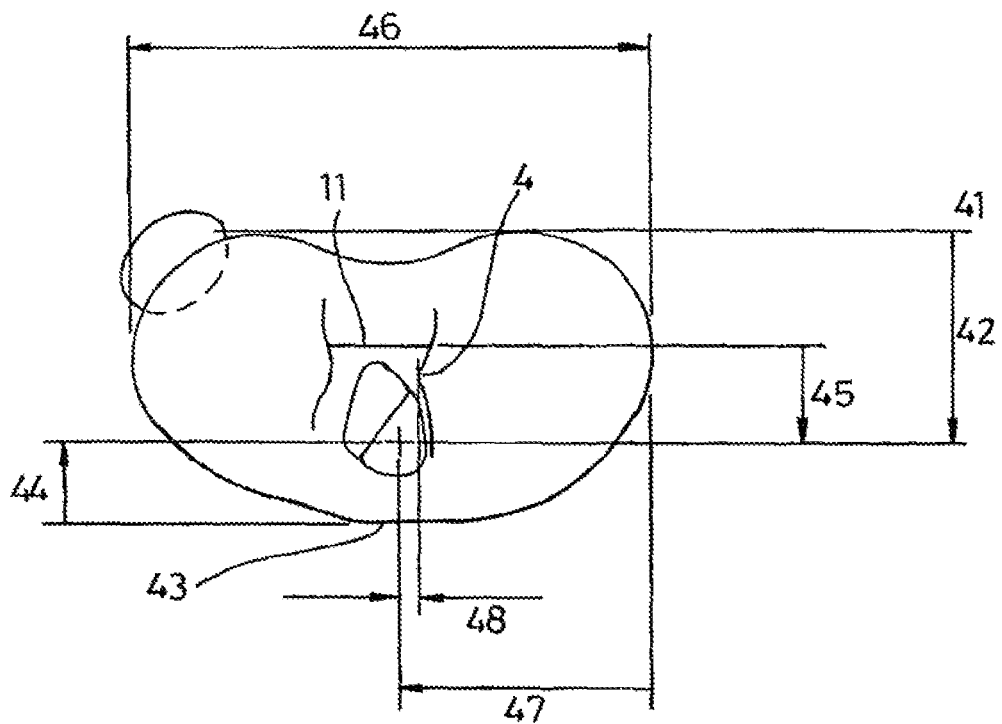
FIG. 4 is a diagram showing various dimensions used to define positions on the tibial plateau of FIG. 1.

The ACL fibre bundle attachments may be located using measurements related to identifiable bony landmarks. These have the advantage over soft tissue landmarks of not being readily deformed or deflected by the application of an instrument, a criticism that applies to instruments that register a fixed distance from the PCL for example. A further advantage of using bony landmarks is that they should persist following ACL rupture, even if the ACL remnants disappear, as occurs in chronic cases. FIG. 4 shows a number of possible methods that can be used to define the position of either the whole ACL attachment to the tibia or, as shown by way of example, the anteromedial fibre bundle, or else the posterolateral fibre bundle. Line 41 is the posterior tibial trans-condylar axis, which the line is passing through the most posterior points on the tibial plateau. This may be used as the datum from which to define the ACL position in an anterior direction 42. Alternatively, or in addition, the ACL may be located in relation to an anterior datum position 43 at the edge of the tibial plateau by measuring the distance 44 posteriorly from this. A preferred method is to locate the ACL by an anterior distance 45 from the transverse inter-spinous ridge 11. The medial-lateral position may be defined in relation to the overall M-L width 46 of the tibial plateau, as a percentage 47 of this width from the medial edge, for example. Alternatively, the ACL attachment position may be located in relation to landmarks within the knee, for example by medial-lateral measurement 48 from the medial spinous process 4. Because it is difficult to locate the summit of the process, it is preferable to measure distances laterally from its steep lateral face. Both anterior-posterior and medial-lateral measurements are needed to define the ACL attachment position on the tibial plateau.

Figure 5:
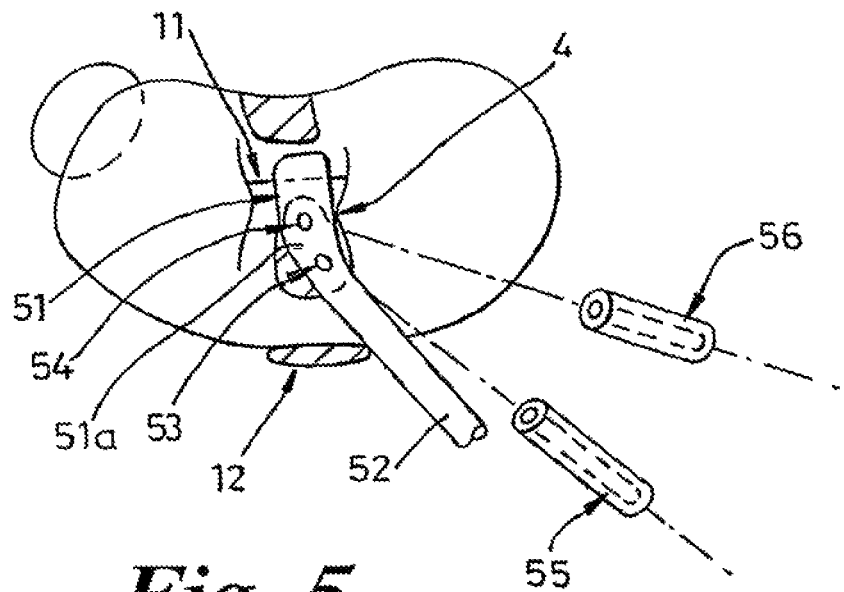
FIG. 5 shows part of a tibial drill guide according to an embodiment of the invention.
Figure 6:
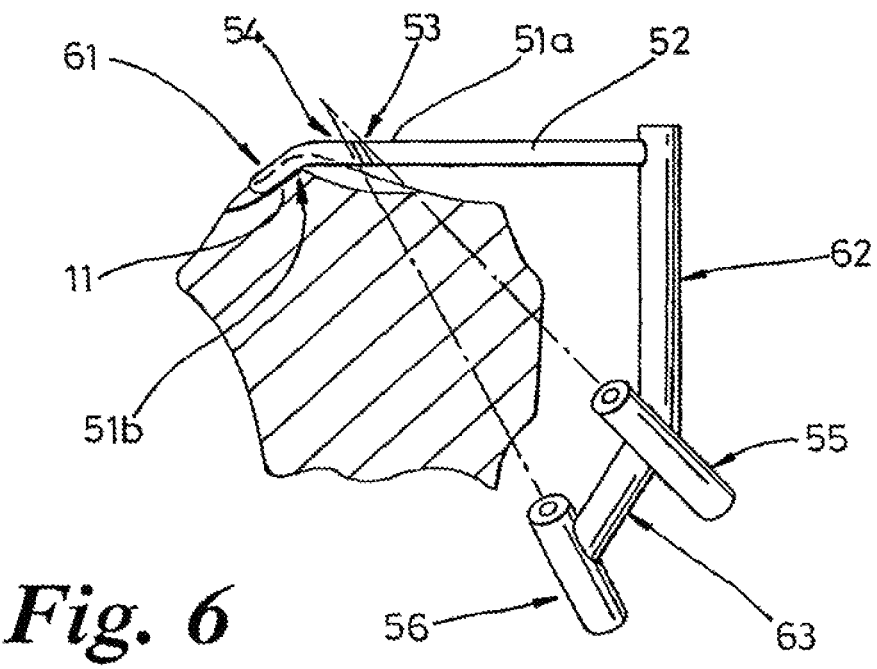
FIG. 6 is a side view of the drill guide of FIG. 5.

Referring to FIGS. 5, 6, a tibial drill guide according to a first embodiment of the present invention is intended to guide the paths of the ACL graft tunnels to the desired location on the tibial plateau, one tunnel for a single-bundle reconstruction, two for double-bundles. The drill guide comprises an intra-articular probe 51, connected to a handle 52 in the form of a shaft. A mounting 62 in the form of another shaft extends at right angles to the handle 52 and supports two drill guides 55, 56 which are interconnected by a joining member 63. The probe 51 has two guide apertures 53, 54 through its main portion 51a. It is also bent through about 45° at its free end to form a locating portion 61 at the tip of the probe which is angled to the main portion with a locating groove 51b extending across the probe 51 between the main portion 51a and the locating portion 61. The underside of the main portion 51a and the locating portion 61 forms a locating surface arranged to locate on the transverse inter-spinous ridge of the tibia as described below. This locating surface is made up of two parts, one formed on the underside of the main portion 51a and the other formed on the underside of the locating portion 61. In this embodiment these two parts are angled at about 45° to each other, but angles from 30° to 75° have been found to function successfully, with angles of 60° or less being preferable, and angles of at least 45° being more preferable. Each of the drill guides 55, 56 is in the form of a tube defining a drill guide aperture, and each of the drill guide apertures is aligned with a respective one of the guide apertures 53, 54 in the probe 51. In use, the intra-articular probe 51 will usually enter the knee joint via a portal at the medial side of the patellar tendon 12. The probe 51 is angled at about 45° to the handle 52 so that if the probe is held to extend in the anterior-posterior direction, the handle 52 extends to the side of the patellar tendon 12. It would be possible to use other portals, lateral to the patellar tendon or through the patellar tendon, with a suitable change of orientation of the handle 52 in relation to the probe 51. The medial side 51c of the probe 51 is located by the surgeon against the lateral aspect of the medial tibial spinous process 4, as shown in FIG. 5. The probe is located in the anterior direction by pulling the angled tip 61 until it engages the back of the transverse ridge 11 so that the locating groove 51b is located on the top of the transverse ridge 11. By this means, the probe 51 is located in both medial-lateral and anterior-posterior directions. The drill locating apertures 53, 54 are placed to receive the tips of guide wires which are aligned by being passed up through the drill guides 55, 56 and drilled up through the tibia, emerging in the correct locations within the ACL bundle attachment areas 9, 10. The drill guide tubes 55, 56 in this case are attached to handle 52 in a fixed relationship. However, they may be adjustably attached so that the angle at which the guide wires are drilled into the tibia can be adjusted. The drill guide tubes 55, 56 are in this embodiment mounted at a compound angle with respect to the anterior-posterior and longitudinal axes of the tibia, i.e. they are at an angle to both of these axes, orientated typically 30 to 70 degrees medial to the anterior-posterior axis and elevated typically 40 to 60 degrees from horizontal, a typical configuration being indicated for anteromedial 55 and posterolateral 56 drill guides in FIGS. 5 and 6.

The drill guides 55, 56 are shown in FIG. 6 with a fixed relationship to the handle 52 and probe tip 61 via the mounting 62 and joining member 63 by way of example only. Adjustment means could allow, for example, the guides 55, 56 to move axially towards the tibial surface, or even to engage the bone using sharpened tips. Alternatively, the orientations could be adjustable so that they can be altered, by means of a pivoting mechanism that ensures that the axes of the guide tubes always point towards the correct points on the surface of the tibial plateau, within the ACL bundle attachment areas 9, 10 and the guide apertures 53, 54.

In a modification to the embodiment described above, the drill guide is arranged for a single bundle reconstruction. In this case the probe 51 only requires a single guide aperture, and only a single drill guide is needed, which again can be fixed or adjustable in position.

Figure 7:
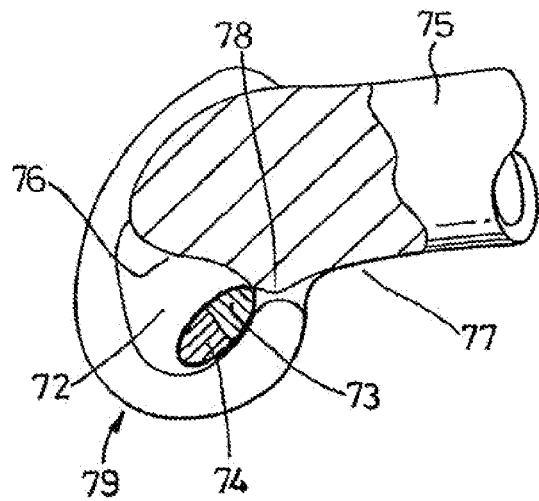
FIG. 7 is a partially sectioned medial-lateral view of a distal femur.
Figure 7A:
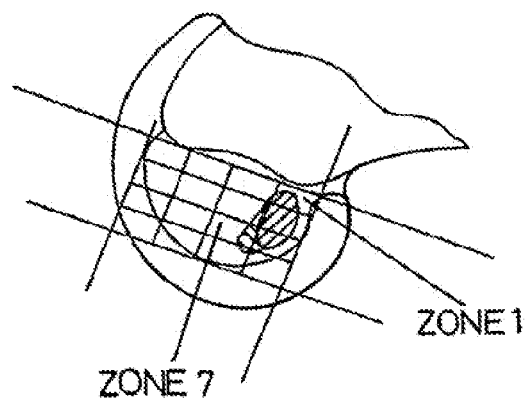
FIG. 7a is a view similar to FIG. 7 including a reference grid for defining ligament attachment positions on the femur.
Figure 8:
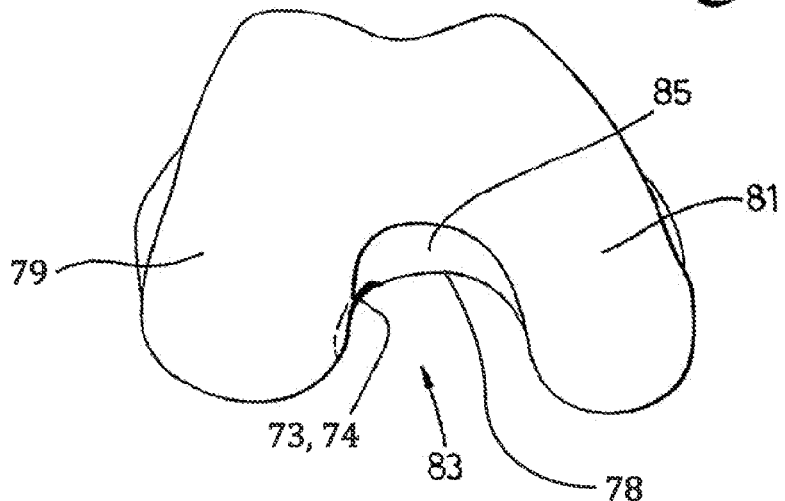
FIG. 8 is an end view of the femur of FIG. 7.

FIGS. 7 and 8 show the gross anatomy of the right distal femur. FIG. 7 is a medial-lateral view, with the bone sectioned on the midline, so that the medial condyle has been removed. The prominent bulges seen in FIGS. 7 and 8 are the medial condyle 81 and lateral condyle 79. The femoral intercondylar notch 83 lies between the condyles 79, 81; the lateral wall 72 of the intercondylar notch is exposed in FIG. 7. The ACL anteromedial fibre bundle attachment area 73 and the ACL posterolateral fibre bundle attachment area 74 are illustrated. The whole attachment area 73, 74 of the ACL is elongated, inclined approximately 35-40 degrees from the axis of the femoral shaft 75. FIG. 8 is an end-view of the femur, as seen by the surgeon when the knee is flexed 90 degrees. It is difficult to see the ACL attachment area clearly in a true axial view, it being on the lateral side-wall of the notch. The region at the top of the intercondylar notch in FIG. 8 is known as the notch 'roof' 85. This is seen as a slightly curved line 76 in the midline section (FIG. 7); the line is seen clearly on a medial-lateral radiograph, when it is known as 'Blumensaat's line'. The junction between the notch roof 85 and the femoral shaft posterior aspect 77 forms a transverse ridge 78 (FIGS. 7, 8, and 9) that is easily located through the intercondylar notch 83. This ridge may be used to locate an ACL drill guide, in a manner akin to that used above, for the transverse interspinous ridge 11 of the tibia. The crest of this ridge is often referred to as the over-the-top position. This 'posterior outlet' of the intercondylar notch is nearly semicircular, so surgeons may define a position around it in "o'clock" positions; 12 o'clock being at the top, etc. . . . . Because the roof line 76 of the notch is at an angle to the axis of the shaft of the femur 75, the roof 85 of the notch is seen sloping downwards in an end-view of the femur. As the surgeon moves distally from the transverse ridge 78 i.e. towards the left in FIG. 7, the clock positions become less accurate, as the roof 85 rises. Thus, an alternative method is to define the "o'clock" positions when looking through the notch 83 parallel to the slope of the roof line 76. Other means to define the attachment areas 73, 74 of the ACL bundles include fitting a circle to the circular outline, as seen in the lateral direction, of the posterior part of the lateral femoral condyle 79 and navigating in anterior-posterior and proximal-distal directions from the centre of the circle. The diameter may be defined as 100%, and the position of the attachment areas defined in percentage terms, thus normalising for various knee sizes. A further method is to define a reference grid on the side wall of the notch, in this case by dividing the lateral side wall of the notch into a rectangular grid as in FIG. 7a. This reference grid is then used to define the ACL attachment positions in percentage terms of height from the roof line 76 of the notch and distance along the notch roof from one end. In the example shown in FIG. 7a, rectangular grid is defined having an upper side defined on the roof line 76, a lower side tangential to the bottom of the side wall 72 of the intercondylar notch, and proximal and distal ends also tangential to the side wall 72 at the junction with the articular cartilage. In this embodiment the grid is divided into sixteen zones, in four rows by four columns. The zones are then numbered from one to sixteen starting with the top section of the most proximal column, counting down that column, and then down successive columns, so that the lowest, most distal zone is number 16.

Figure 9:
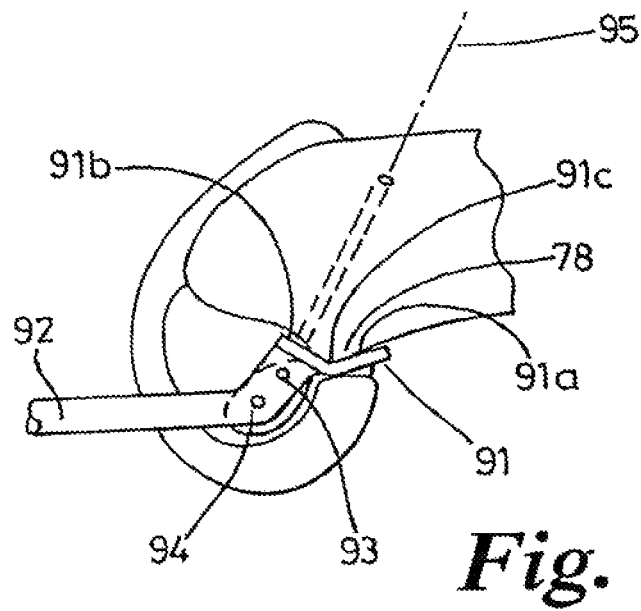
FIG. 9 is a side view of part of a drill guide according to a second embodiment of the invention.
Figure 10:
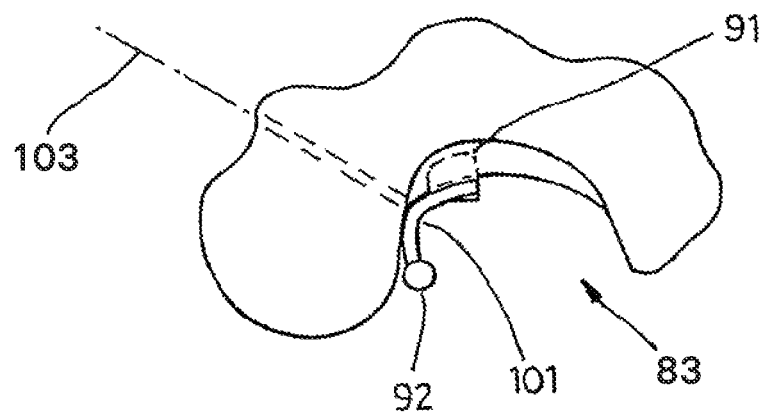
FIG. 10 is an end view of the drill guide of FIG. 9.

One example of how the bony geometry may be used to locate a femoral tunnel drill guide is provided by the drill guide according to a further embodiment of the invention which is shown in FIGS. 9 and 10. This instrument may include an angled probe tip 91 which has two locating surfaces 91*a*, 91*b* which are angled relative to each other to define a locating groove 91*c* where they join. This forms a deep-shallow locating mechanism arranged to locate on the transverse ridge 78 in the intercondylar notch 83. The probe tip 91 is joined to a curved side piece 101 which forms a high-low locating mechanism arranged to locate against the lateral side wall 72 and roof 85 of the intercondylar notch. The probe has formed through it, at one end of the curved side piece 101 two drill guide apertures 93, 94 which are arranged to be located at the centres of the ACL attachment areas 73, 74 when the locating mechanisms are located on their respective bone features. A handle 92 is attached to the curved side piece 101 and is arranged to extend parallel to the femoral shaft when the probe is correctly located.

In use, the angled probe tip 91 may be brought into contact with the transverse ridge 78 at the posterior outlet of the intercondylar notch. This feature is common to many 'offset' drill guides. However, they do not control position around the notch, and the surgeon must make a subjective estimate of the correct "o'clock" position. In this embodiment of the present invention, the curved side piece 101 is also located around the lateral side-wall 72 of the notch. This provides full location of the drill guide apertures 93, 94 in two dimensions on the surface of the bone, and hence in three dimensions in total.

The probe may include only one hole rather than two if it is designed for single bundle reconstruction.

Figure 11:
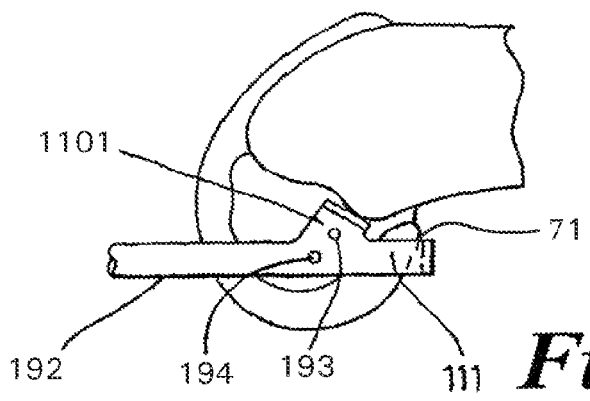
FIG. 11 is a side view of part of a drill guide according to a further embodiment of the invention.
Figure 12:
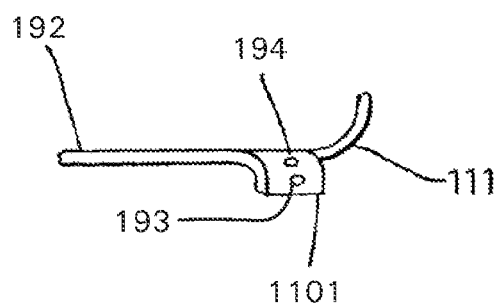
FIG. 12 is a top view of the drill guide of FIG. 11.

In a further embodiment shown in FIG. 11, the angled probe tip 91 of FIG. 9 is replaced by a curved locating extension 111, that is arranged to wrap around the back surface 71 of the femoral condyle 79, so that pulling the handle 192 will locate holes 193, 194 correctly in the shallow-deep direction as seen from the distal end of the femur. The instrument of FIGS. 11 and 12 may still incorporate a curved side piece 1101 that rests against the roof 85 of the notch 83, in order to control the height of the holes 193, 194.

Figure 13:
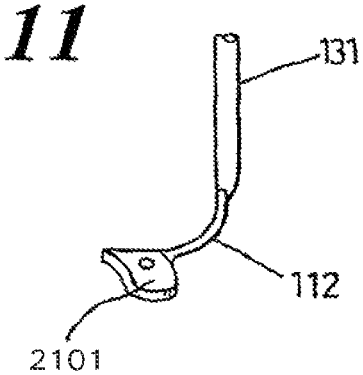
FIG. 13 is a top view of part of a drill guide according to a further embodiment of the invention.

Referring to FIG. 13 in another embodiment, a handle 131 similar to the handle 92 in FIG. 11 is located for positioning at the front of the knee. The handle 131 is attached to a curved probe tip 112 that is in turn attached to a curved side piece 2101. The handle 131 will extend in the lateral direction when the curved probe tip 112 is correctly located against a femur. The instrument configured in the manner shown in FIG. 13 may be introduced through a postero-lateral incision. The key feature of all these design variations is that the drilling target, represented by holes 93, 94, 193, 194, is always located in two dimensions across the surface of the bone at the area of the natural ACL attachment, i.e. shallow-deep and high-low as perceived by the surgeon.

In order to aid correct alignment of the intra-articular part of the drill guide, the handle 52 for tibia or handle 92, 131, 192 for femur, will be adapted to aid the surgeon's perception of orientation. The graft tunnels are normally drilled at compound angles to the axes of the bones, i.e. offset from both the anterior-posterior direction and offset from the perpendicular to the main longitudinal axis of the bone. This is for reasons of surgical access, avoiding vulnerable anatomical structures, and maintaining sufficient tunnel length. In the tibia, the tunnels are normally drilled from outside-in, in approximately the orientations shown in FIGS. 5 and 6. That is, so that they enter the tibia on the antero-medial aspect, from a point typically 2-6 cm distal to the tibial plateau, angled at approximately 40-60 degrees elevation, so that the tunnels are centred within the ACL attachment areas as desired. A similar situation occurs at the femur, except that the tunnels can be drilled inside-out or outside-in. For inside-out drilling, the knee is usually flexed as far as possible and the guidewire is introduced into the knee through an antero-medial portal, beside the patellar tendon. It then slants across the interior of the knee to the target holes 93, 94, 193, 194, passes through them and is then drilled into the lateral femoral condyle, along the paths shown by way of example as 95 in FIGS. 9 and 103 in FIG. 10, often until it emerges on the antero-lateral aspect of the thigh. In a similar inside-out method, the guidewire is passed into the knee through a tibial graft tunnel that has been drilled first. For inside-out femoral drilling, the surgeon may simply place the tip of the guidewire through holes 93, 94, 193, 194 by hand; no drill guide is needed. Conversely, for outside-in femoral drilling, the instrument body must be extended so that it passes around, from handle 92, 192, or 131, to the lateral aspect of the knee. Here, there must be guide tubes or barrels, akin to those 55, 56 shown in FIGS. 5 and 6, to ensure that the guidewire passes along a fixed axis 95, 103 through the femur until it emerges into the knee joint at the desired graft attachment areas 73, 74 and then may pass into hole 93, 94, 193, 194 in the locating piece within the knee.

In order to ensure that the intra-articular parts of the instruments have the correct alignment in the knee, the handles that enter the knee from the anterior aspect 52, 92, 192 will be adapted to aid alignment. This will depend on the surgeon's perceptions of symmetry and of parallelism. In some embodiments, the instrument includes an alignment member or handle 62 attached to the probe so that, when it is held parallel to the long axis of the tibia, as shown in FIG. 6, with the knee at a fixed 90 degrees flexion angle, and on the midline sagittal plane i.e. so that it is directly in front of the tibia as can best be seen in FIG. 14, then the intra-articular parts 51, 61 will have the correct orientation. This will particularly aid control of the "o'clock" position of side pieces 101, 1101, 2101 of the femur drill guide and, hence, the height of the holes for attaching the reconstructed ligament to the femur.

Figure 14:
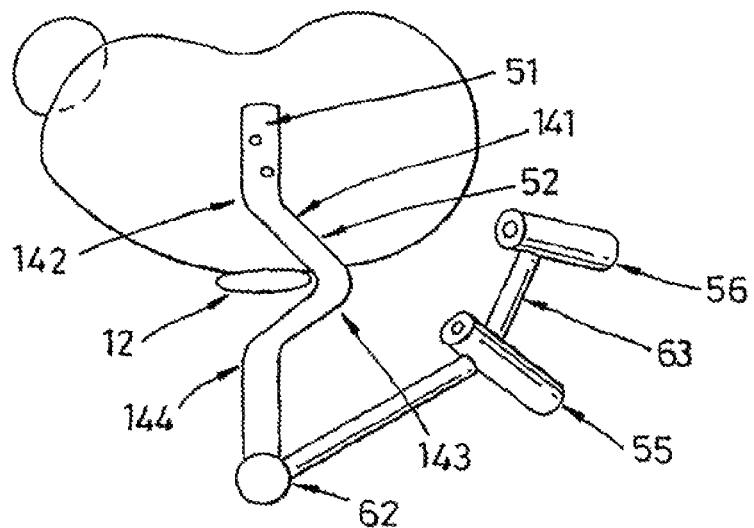
FIG. 14 is a top view of a drill guide according to a further embodiment of the invention.

In one embodiment as shown in FIG. 14, the handle 52 of a tibial drill guide incorporates a curved or angled part 141, that is arranged to pass around, i.e. to one side of, the patellar tendon 12 when the probe tip is in the correct position for drilling and the alignment handle 62 is located on the anterior midline of the tibia. The curved part 141 incorporates three angles or bends 142-144. A similar arrangement may be used to ensure the correct orientation of the femoral intra-articular instrument, with or without drill guides held in fixed relationships to it for outside-in drill axis control.

This embodiment therefore incorporates bends, so that the handle passes around the patellar tendon. The handle is brought onto the midline so that it can be used to control/judge the orientation.

If the instrument is arranged to be introduced into the knee from the posterolateral direction as shown in FIG. 13, then it may be adapted by a joining part that passes around the lateral aspect of the knee to the anterior aspect, there joining to a handle arranged to be aligned parallel to the axis of the tibia similar to that of FIG. 14.

Figure 15:
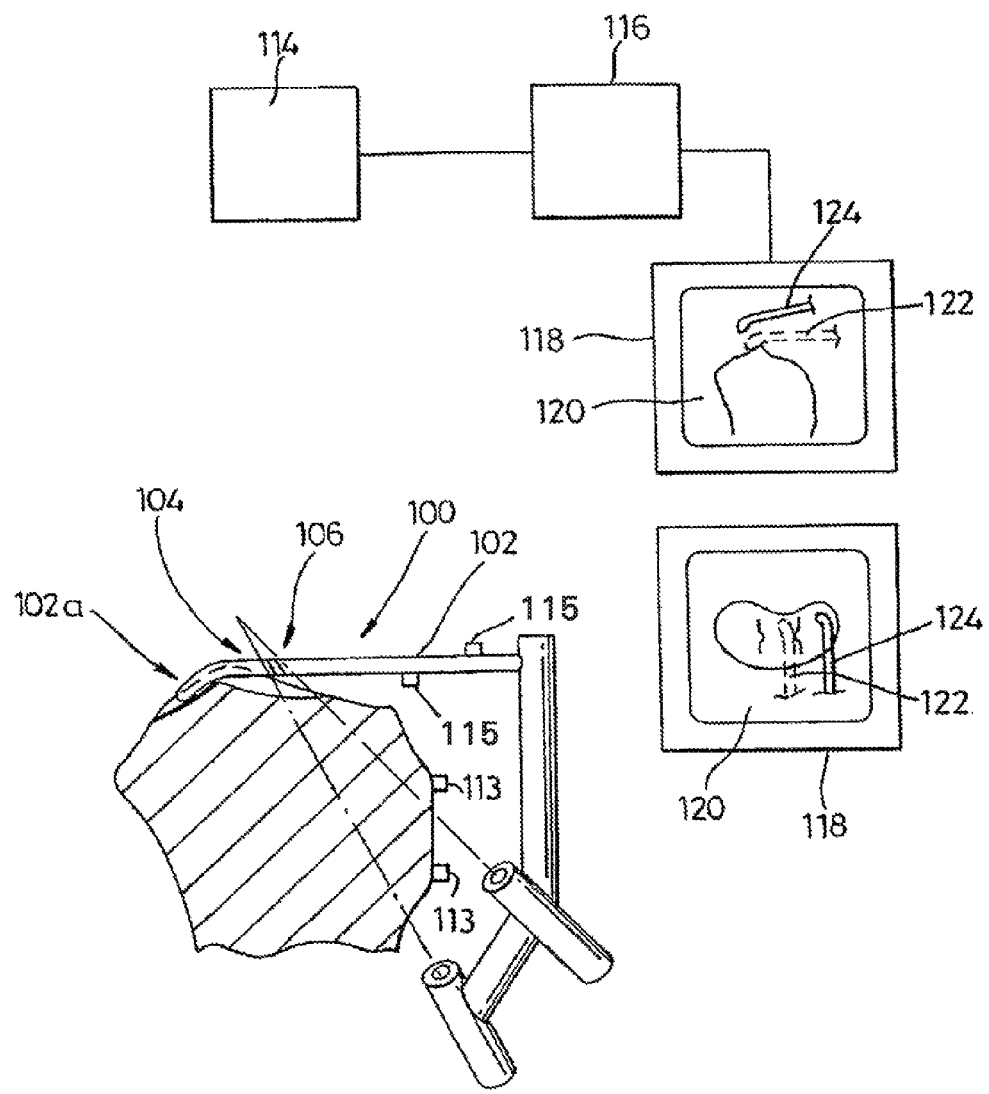
FIG. 15 is a diagram of a computer guidance system according to a further embodiment of the invention.

Referring to FIG. 15 a further embodiment of the invention comprises a computer controlled navigation system for guiding a surgeon in the use of a drilling guide. This system comprises a drilling guide 100 comprising a probe 102 with two drill guide apertures 104, 106 through it, and two drill guide tubes 108, 110 supported in alignment with the guide apertures 104, 106 in a similar manner to the guide of FIG. 6. The probe 102 of the drill guide has a number of locating markers 115 attached to it and a locating system 114 is provided that can locate the absolute positions of each of the markers 115 in space, and hence the position and orientation of the probe. This could, for example, be the BrainLab (Germany) system that uses reflective markers and stereo cameras. Similarly, the bones (femur and tibia) will have markers 113 attached such that the computer can calculate their positions in 3D space. The locating system is connected to a computer 116 which in turn is connected to a display 118. The computer 116 has stored in it data defining models of a range of different possible sizes and shapes of femur and tibia based on measurements of real bone samples. It is arranged to provide instructions on the display 118 to instruct the surgeon.

In use, the system first provides instructions to the surgeon via the display 118 to move the tip 102a of the probe 102 to various points on the bone that is to be operated on. These instructions can identify a number of easily identifiable points on the bone that the surgeon can touch with the probe tip 102a, or they may just instruct the surgeon to move the probe tip 102a over the surface of parts of the bone. As the probe is moved to different locations on the bone, the computer 116 monitors the different positions of the tip 102a of the probe and stores these as a set of position data. From this position data, the computer 116 is then arranged to build up a model of the surface of the bone to be operated on. This model includes a number of features which can be used to locate the desired positions of the drillings for ACL reconstruction, in this case including the positions of the spinous processes 4, 5, the inter-spinous fossa 6, the inter-spinous ridge 11 on the tibia, and the condyles 79, 81, inter-condylar notch 83 and the transverse ridge 78 on the femur. Clearly the more actual points on the bone surface that are located by the probe, the more accurate the model of the bone will be.

Once the model has been defined, the computer is arranged to identify the positions in real space of the bone features to be used for drilling location, and to determine from those positions the desired positions in real space of the drillings. This is done using stored data relating to the actual positions of the ACL attachments, relative to the selected bone features, on the femur and tibia for a number of bone samples. From these desired drilling positions and data stored in the computer relating to the shape of the probe and the positions of the drill guide apertures in the probe, the computer 116 determines the desired position in real space for the drill guide 102 to guide a drill or guide wire to the desired locations on the bone. The computer 116 then generates an image 120, with guide outputs in the form of guide markings 122 on it indicating the desired position of the guide 102, and guide position markings 124 showing the actual position of the guide 102. In this case two images 120 are generated and displayed simultaneously showing the bone and probe 102 from different angles so that the surgeon can better determine the absolute position of the probe relative to the desired position. By watching the images on the display 118 the surgeon can move the guide 100 until the guide position markings 124 indicate that the guide 100 is in the desired position. The guide 100 can then be held still while the drillings are made.

Another variant of this system will have a single probe 100 that has tracking markers 115 used solely to digitise the bone features and not featuring drill guides. When the bone geometry has been determined, a drill with tracking features attached is placed on the outer surface of the knee. An image on the computer screen guides the surgeon such that the drill is oriented towards the correct attachment position within the knee.

The features selected for locating the drilling positions are selected to provide location in two dimensions on the surface of the bone. For example the same features can be used for the tibia and the femur as described above to provide physical location of the probe. However, it will be appreciated that with this type of system the method of locating the desired position of the drillings on the surface of the bone can be considerably more complex than using two distances or angles from respective landmark features. For example the ideal drilling position can be defined by an optimisation process that determines an optimum position using a large number of different distances and directions from a number of different points on the bone. However, such a location method will still enable the optimum drilling position to be defined in two dimensions on the bone surface.

In a further embodiment, the model of the bone is derived not from contact with a probe but by means of an imaging system which includes a number of imaging devices, such as fluoroscopic imaging devices arranged to image the knee joint from different angles. This allows a 3-dimensional computer model of the bone to be built up which can be used to determine the optimum drilling positions and therefore the optimum drill guide position. Guide markings can then be superimposed on the image to indicate to the surgeon where the drill guide should be located, and a real-time image of the actual probe used can then be provided and monitored by the surgeon to determine when the probe is in the desired position.

Measurement of Femoral ACL Attachment

In order to determine the optimum locations of drillings for attaching reconstructed ACLs a number of measurements of cadaver knees were taken. The aim was to describe the anatomical locations of the femoral attachment of the anterior cruciate ligament, for both its anteromedial AM and posterolateral PL bundles so that the drillings can be placed in corresponding locations. A number of different measurement techniques were used to achieve the most information concerning the attachment of the ACL.

22 human cadaver knees with intact anterior cruciate ligaments were measured. The femoral attachments of the two bundles were identified and marked. Digital photographs were taken and the attachments were measured and described in terms of the o'clock positions parallel to the femoral long axis and parallel to the roof of the intercondylar notch. The centres of the bundles were measured in a high-low and a superficial-deep manner referencing from the centre of the posterior femoral condyle, and with respect to their positions within a reference grid system as shown in FIG. 7a. When looking parallel to the notch roof, the bulk of the AM bundle was attached between 9 and 11 o'clock and the bulk of the PL bundle between the 8 and 9:30 o'clock positions. The AM bundle was consistently found in zone 1 of the quadrant method and the PL bundle in zone 7. Using the diameter of the posterior femoral condyle reference method, the centre of the AM bundle should preferably be located in the range 60 to 75% in a shallow-deep direction and in the range 45-60% in a high-low direction. The PL bundle should preferably be located in the range 40-70% in a shallow-deep direction, and 40-70% in a high-low direction. The attachment was orientated at 37° to the femoral long axis.

Measurement of Tibial ACL Attachment

The aim was to find a measurement method that would lead to the most consistent placement of tibial tunnels for arthroscopic ACL reconstruction. This should be based on a reliable anatomic landmark to avoid a wide variation in positions between knees. It was found that this could be done by measuring from the "over-the-back" position, i.e. the top of the transverse inter-spinous ridge, in an anterior direction, and from the lateral surface of the medial tibial spine in a lateral direction.

55 specimens were used and the anterior cruciate ligament attachments were measured in relation to various bony landmarks. Wide variation in measured values was found when using the posterior tibial axis, the anterior tibial surface and the tip of the medial tibial spine as reference points. The least variation in measured values occurred between the tibial interspinous "over-the-back" position and the posterior limit of the anterior cruciate ligament attachment. The over-the-back landmark also led to the least variation in values with respect to the centres of the fibre bundles. The attachments of the posterolateral and anteromedial bundles were 8 to 12 mm and 12 to 20 mm respectively anterior to the over-the-back landmark and in the range of 3 to 7 mm lateral to the lateral face of the medial tibial spine. In order to avoid notch impingement in the extended knee, the graft tunnels should be placed posteriorly in the ACL tibial fibre bundles; the PL tunnel in the range 8 to 10 mm and the AM tunnel 14 to 19 mm anterior to the transverse intercondylar ridge. In relation to the posterior tibial axis, these measurements are 24 to 35 mm for the PL bundle and 31 to 44 mm for the AM bundle attachment. The corresponding tunnels should be in the ranges 23 to 34 mm for the PL and 30 to 44 mm for the AM tunnel. The distances from the posterior surface of the tibia and the "over-the-back" position to the centres of the bundle attachments correlated significantly with the ML width and the AP depth of the tibial plateaux, as did the distances to the centres of the tunnel positions.

What is claimed is:

1. An instrument for locating an attachment position for a reconstructed anterior cruciate ligament (ACL) in a femur comprising:
   a handle;
   a side piece comprising:
      a first surface shaped to fit at least in part against a lateral side wall of an intercondylar notch to locate the instrument relative to the femur, and
      a second surface configured to contact a roof of the intercondylar notch at the same time the first surface is at least in part against the lateral side wall of the intercondylar notch to locate the instrument relative to the femur; and
   a tip arranged to wrap around a back surface of a condyle of the femur and contact the back surface of the condyle at the same time the first surface is at least in part against the lateral side wall of the intercondylar notch and the second surface is contacting the roof of the intercondylar notch to locate the instrument relative to the femur;
   wherein there is a hole in the side piece that defines the attachment position for the reconstructed ACL.

2. The instrument of claim 1 wherein the side piece is coupled to the handle.

3. The instrument of claim 1 wherein the side piece is coupled to the tip.

4. The instrument of claim 1 wherein the tip is coupled to the handle.

5. The instrument of claim 1 wherein the hole is arranged to be located at the centre of the reconstructed ACL attachment position.

6. The instrument of claim 1 wherein there are two holes in the side piece that define one or more attachment positions for the reconstructed ACL.

7. The instrument of claim 6 wherein the two holes are arranged to be respectively located at the centres of two reconstructed ACL attachment positions.

8. The instrument of claim 1 wherein the linear and rotational relationships between the first surface, the second surface, and the tip are defined by accumulation of anatomical measurement data from a statistically significant number of femurs.

9. An instrument for locating an attachment position for a reconstructed anterior cruciate ligament (ACL) in a femur comprising:
   a handle;
   a side piece comprising:
      a first surface shaped to fit at least in part against a lateral side wall of an intercondylar notch to locate the instrument relative to the femur, and
      a second surface configured to contact a roof of the intercondylar notch at the same time the first surface is at least in part against the lateral side wall of the intercondylar notch to locate the instrument relative to the femur; and
   a tip with a contact surface directed at least in part toward the second surface such that at least part of the contact surface forms an angle of less than 180 degrees with the second surface, wherein the contact surface is configured to contact a part of the femur at the same time the first surface is at least in part against the lateral side wall of the intercondylar notch and the second surface is contacting the roof of the intercondylar notch to locate the instrument relative to the femur;
   wherein there is a hole in the side piece that defines the attachment position for the reconstructed ACL.

10. The instrument of claim 9 wherein the side piece is coupled to the handle.

11. The instrument of claim 9 wherein the side piece is coupled to the tip.

12. The instrument of claim 9 wherein the tip is coupled to the handle.

13. The instrument of claim 9 wherein the part of the femur the contact surface is configured to contact is a transverse ridge of the femur.

14. The instrument of claim 9 wherein the part of the femur the contact surface is configured to contact is a back surface of a condyle of the femur.

15. The instrument of claim 9 wherein the hole is arranged to be located at the centre of the reconstructed ACL attachment position.

16. The instrument of claim 9 wherein there are two holes in the side piece that define one or more attachment positions for the reconstructed ACL.

17. The instrument of claim 16 wherein the two holes are arranged to be respectively located at the centres of two reconstructed ACL attachment positions.

18. The instrument of claim 9 wherein the linear and rotational relationships between the first surface, the second surface, and the tip are defined by accumulation of anatomical measurement data from a statistically significant number of femurs.

19. A method of locating an attachment position for a reconstructed anterior cruciate ligament (ACL) in a femur comprising:
   passing a tip of a locating instrument around a condyle of the femur by moving the locating instrument distally and laterally;
   moving the locating instrument proximally to bring the tip of the locating instrument into contact with a back surface of the condyle;

contacting a first surface of a side piece of the locating instrument against a lateral side wall of an intercondylar notch; and contacting a second surface of the side piece of the locating instrument against a roof of the intercondylar notch at the same time the first surface is contacting the lateral side wall of the intercondylar notch and the tip of the locating instrument is contacting the back surface of the condyle to locate the instrument relative to the femur.

20. The method of claim 19, further comprising marking the attachment position for a reconstructed ACL through a hole in the side piece of the locating instrument.

21. The method of claim 19, further comprising drilling a hole in the femur through a hole in the side piece of the locating instrument.

22. The method of claim 21 wherein the act of drilling a hole in the femur includes drilling a hole with a guidewire.

23. The method of claim 22 wherein the act of drilling a hole with a guidewire includes drilling inside-out by placing a distal end of the guidewire through the hole in the side piece of the locating instrument and drilling.

24. The method of claim 22 wherein the act of drilling a hole with the guidewire includes drilling outside-in by drilling through the femur and into the hole in the side piece of the locating instrument with the aid of a drill guide.

* * * * *